(12) United States Patent
Robichaud et al.

(10) Patent No.: US 10,588,721 B2
(45) Date of Patent: Mar. 17, 2020

(54) ATTACHMENT SYSTEM FOR REMOVABLE DENTAL PROSTHESIS AND DENTAL IMPLANT ABUTMENT

(71) Applicant: PANTHERA DENTAL INC., Quebec (CA)

(72) Inventors: Jean Robichaud, Quebec (CA); Florent Miquel, Sainte-Catherine-de-la-Jacques-Cartier (CA)

(73) Assignee: PANTHERA DENTAL INC., Québec, Québec (CA)

( * ) Notice: Subject to any disclaimer, the term of this patent is extended or adjusted under 35 U.S.C. 154(b) by 67 days.

(21) Appl. No.: 14/717,508

(22) Filed: May 20, 2015

(65) Prior Publication Data

US 2015/0335401 A1 Nov. 26, 2015

Related U.S. Application Data

(60) Provisional application No. 62/000,772, filed on May 20, 2014.

(51) Int. Cl.
| | |
|---|---|
| *A61C 8/00* | (2006.01) |
| *A61C 13/34* | (2006.01) |
| *A61C 13/277* | (2006.01) |
| *A61C 13/271* | (2006.01) |
| *A61C 13/00* | (2006.01) |

(52) U.S. Cl.
CPC ............ *A61C 8/0063* (2013.01); *A61C 8/006* (2013.01); *A61C 8/0018* (2013.01); *A61C 8/0048* (2013.01); *A61C 8/0053* (2013.01); *A61C 8/0062* (2013.01); *A61C 8/0074* (2013.01); *A61C 13/0003* (2013.01); *A61C 13/26* (2013.01); *A61C 13/277* (2013.01); *A61C 13/34* (2013.01)

(58) Field of Classification Search
CPC ..... A61C 8/005; A61C 8/0048; A61C 8/0053; A61C 8/0068; A61C 13/2656
USPC .......................................................... 433/173
See application file for complete search history.

(56) References Cited

U.S. PATENT DOCUMENTS

| | | |
|---|---|---|
| 5,030,095 A | 7/1991 | Niznick |
| 5,195,891 A | 3/1993 | Sulc |

(Continued)

*Primary Examiner* — Sean M Michalski
*Assistant Examiner* — Matthew P Saunders
(74) *Attorney, Agent, or Firm* — Merchant & Gould P.C.

(57) ABSTRACT

A dental prosthesis attachment system is for an endosseous dental implant. The dental prosthesis attachment system includes: a removable dental prosthesis; a dental prosthesis portion secured to the removable dental prosthesis; and a dental implant portion securable to the dental implant and removably engageable with the dental prosthesis portion. The dental prosthesis portion includes an open-ended dental prosthesis sleeve having an outer surface and an inner cavity. The outer surface is secured to the dental prosthesis and the inner cavity is lined with a retention material defining an inner peripheral wall having at least one of a protrusion and a recess. The dental implant portion includes an attachment pillar removably insertable within the inner cavity of the dental prosthesis portion. The attachment pillar has a peripheral wall provided with at least one of a protrusion and a recess removably interlocked with the at least one of the recess and the protrusion on the inner peripheral wall of the inner cavity.

21 Claims, 18 Drawing Sheets

(56) References Cited

U.S. PATENT DOCUMENTS

| | | | |
|---|---|---|---|
| 5,417,570 A | 5/1995 | Zuest et al. | |
| 5,427,527 A | 6/1995 | Niznick et al. | |
| 5,556,280 A * | 9/1996 | Pelak | A61C 8/0048 433/172 |
| 5,662,473 A | 9/1997 | Rassoli et al. | |
| 5,931,674 A | 8/1999 | Hanosh et al. | |
| 6,030,219 A * | 2/2000 | Zuest | A61C 8/0048 433/172 |
| 6,287,115 B1 | 9/2001 | Lustig et al. | |
| 6,663,388 B1 * | 12/2003 | Schar | A61C 8/005 433/173 |
| 7,785,108 B2 | 8/2010 | Tache et al. | |
| 8,459,994 B2 * | 6/2013 | Freilich | A61C 8/0048 433/173 |
| 2005/0214717 A1 * | 9/2005 | Freilich | A61C 8/0048 433/180 |
| 2009/0075235 A1 * | 3/2009 | Letcher | A61C 8/0048 433/173 |
| 2009/0117520 A1 * | 5/2009 | Kikuchi | A61C 8/0081 433/174 |
| 2009/0298013 A1 * | 12/2009 | Baruc | A61C 8/005 433/174 |
| 2010/0075277 A1 * | 3/2010 | Wils | A61C 8/0068 433/193 |
| 2010/0183998 A1 * | 7/2010 | Poirier | A61C 1/084 433/72 |
| 2010/0330529 A1 * | 12/2010 | Shalom | A61C 8/005 433/173 |
| 2011/0053114 A1 * | 3/2011 | Shimoda | A61C 7/36 433/173 |
| 2011/0097687 A1 * | 4/2011 | Engman | A61C 8/005 433/174 |
| 2012/0003606 A1 * | 1/2012 | Fischler | A61C 8/0048 433/141 |
| 2012/0077151 A1 | 3/2012 | Nary Filho et al. | |
| 2012/0088208 A1 * | 4/2012 | Schulter | A61C 8/0001 433/173 |
| 2012/0322030 A1 * | 12/2012 | Fromovich | A61C 8/005 433/173 |
| 2013/0209958 A1 * | 8/2013 | Benz | A61C 8/005 433/173 |
| 2014/0106303 A1 * | 4/2014 | Giasson | A61C 8/0048 433/173 |
| 2014/0178839 A1 * | 6/2014 | Berger | A61C 13/2255 433/173 |

* cited by examiner

ATTACHMENT SYSTEM FOR REMOVABLE DENTAL PROSTHESIS AND DENTAL IMPLANT ABUTMENT

CROSS-REFERENCE TO RELATED APPLICATIONS

This application claims priority under 35 USC § 119(e) of U.S. provisional patent application 62/000,772 filed on May 20, 2014, the specification of which is hereby incorporated by reference.

TECHNICAL FIELD

The present invention relates to the field of dental prostheses and, more particularly, to attachment systems for attaching removable dental prostheses, such as removable dentures, to permanent dental implants.

BACKGROUND

Dental prostheses such as dentures can be permanently fixed to or removable from dental implants or existing teeth or roots. For instance, for permanently fixed dentures, the denture, including an artificial gum and teeth structure, is fixed to implants, anchored in the mandible or maxilla osseous portions, and/or existing teeth or roots.

Removable dentures can be attached in several manners. For instance, the denture can include a locking device adapted to lock the denture onto the crown of a tooth. Dentures can also be removably attached to a permanent implant structure. The implant structure typically includes one or several pins implanted directly into the osseous material of the mandible or maxilla. It can further include a metallic arch or bar formed to bridge individual pins together. The denture includes an artificial gum structure adapted to fit snugly over the arch and an attachment device for attaching the denture to the arch. For instance, the attachment system can be achieved by male/female members that are releasable from one another when it is desired to remove the denture from the mandible. A single surface of interference is typically provided between the male and female members, so as to retain the denture onto the mandible. However, due to the pressures exerted during chewing (i.e., high magnitude, from any direction), denture attachment systems having single surfaces of interference can be subjected to the undesired detachment of the denture from the mandible.

SUMMARY

It is therefore an aim of the present invention to address the above mentioned issues.

According to a general aspect, a dental prosthesis attachment system for an endosseous dental implant is provided. The attachment system includes a removable dental prosthesis, at least one dental prosthesis portion, and a dental implant portion. The dental prosthesis portion is secured to the removable dental prosthesis and includes an open-ended dental prosthesis sleeve having an outer surface and an inner cavity, the outer surface being secured to the dental prosthesis and the inner cavity being lined with a retention material defining an inner peripheral wall having at least one of a protrusion and a recess. The dental implant portion is securable to the dental implant and removably engageable with the dental prosthesis portion. It includes an attachment pillar removably insertable within the inner cavity of the dental prosthesis portion. The attachment pillar has a peripheral wall provided with at least one of a protrusion and a recess removably interlockable with the at least one of the recess and the protrusion on the inner peripheral wall of the inner cavity.

In an embodiment, the dental prosthesis portion comprises an outer rigid sleeve and an inner flexible sleeve removably fitted therein, the outer rigid sleeve providing the outer surface of the dental prosthesis portion, and the inner flexible sleeve comprising the retention material and providing the inner peripheral wall of dental prosthesis portion. The outer rigid sleeve can comprise an inner wall and the inner flexible sleeve can comprise an outer wall, the inner wall of the outer rigid sleeve being provided with at least one of a recess and a protrusion, and the outer wall of the inner flexible sleeve being provided with at least one of a recess and a protrusion engageable with the at least one of the recess and the protrusion on the inner wall of the outer rigid sleeve. The inner wall of the outer rigid sleeve can be provided with spaced-apart peripheral recesses and the outer wall of the inner flexible sleeve can be provided with complementary shaped spaced-apart peripheral protrusions. The outer surface of the dental prosthesis portion can comprise at least one of a recess and a protrusion, defining an interference surface between the outer surface and a body of the dental prosthesis. The outer surface of the dental prosthesis portion can comprise a plurality of spaced-apart peripheral protrusions. The at least one of the recess and the protrusion on the outer surface of the dental prosthesis portion can be aligned with the at least one of the recess and the protrusion on at least one of: the inner wall of the outer rigid sleeve, the outer wall of the inner flexible sleeve and the inner peripheral wall in the inner cavity.

In an embodiment, the dental prosthesis attachment system further comprises an implant abutment secured to the dental implant, and a dental prosthesis engagement section removably secured to the implant abutment, the dental prosthesis engagement section including a base portion from which the attachment pillar extends, the base portion of the dental prosthesis engagement section being provided with a cavity having an open end fitted over the implant abutment. The implant abutment can comprise a head portion, a base portion and an intermediate portion extending therebetween, the head portion comprising a pillar abutment flange abutting against the base portion of the dental prosthesis engagement section, and the base portion comprising an implant abutment flange abutting against the dental implant. The pillar abutment flange can be obliquely angled relative to the implant abutment flange, thereby positioning the attachment pillar to extend from the base portion of the implant abutment at an oblique angle. The cavity in the base portion of the dental prosthesis engagement section and the head portion of the implant abutment can be removably interlocked with one another via a threaded connection.

In an embodiment, the removable dental prosthesis comprises a removable denture having a body defining a gum receiving cavity. The dental prosthesis attachment system can further comprise an attachment bar permanently embedded within the removable denture, the attachment bar comprising a plurality of dental prosthesis portions, each having an open-ended dental prosthesis sleeve accessible through the gum receiving cavity. The outer surface of the dental prosthesis sleeve can comprise an outwardly extending pillar base abutment flange abutting against the dental implant portion when engaged together.

In an embodiment, the implant abutment comprises an open-ended channel extending therethrough, the open-ended channel being sized to receive a fastener which secures the implant abutment to the dental implant.

In an embodiment, the retention material comprises a resilient synthetic polymer conforming to a shape of the peripheral wall of the attachment pillar.

In an embodiment, the inner peripheral wall of the inner cavity is provided with a plurality of spaced-apart peripheral protrusions and the peripheral wall of the attachment pillar is provided with a plurality of spaced-apart complementary shaped peripheral recesses.

In an embodiment, the dental prosthesis attachment system comprises a plurality of dental prosthesis portions and a plurality of dental implant portions, each one being securable to a respective one of dental implants, the plurality of dental implant portions being removably engageable with a respective one of dental prosthesis portions.

According to another general aspect, a kit for attaching a dental prosthesis to an endosseous dental implant is provided. The kit includes a dental prosthesis and a dental implant portion. The dental prosthesis portion is securable to the dental prosthesis and includes an open-ended dental prosthesis sleeve having an outer surface and an inner cavity. The outer surface is securable to the dental prosthesis and the inner cavity is lined with a retention material defining an inner peripheral wall having at least one of a protrusion and a recess. The dental implant portion is securable to the dental implant and removably engageable with the dental prosthesis portion. It includes an attachment pillar sized and shaped for removably fitting within the inner cavity of the dental prosthesis portion. The attachment pillar has a peripheral wall provided with at least one of a protrusion and a recess removably interlockable with the at least one of the recess and the protrusion on the inner peripheral wall of the inner cavity.

According to still another general aspect, a removable denture is provided. The denture includes a denture body with a gum receiving cavity, and at least one dental prosthesis attachment sleeve. The sleeve is housed within the denture body and has an outer surface and an inner surface. The outer surface is secured to the dental prosthesis and the inner cavity is open-ended and accessible through the gum receiving cavity. The inner cavity is lined with a retention material defining an inner peripheral wall having at least one of a protrusion and a recess configured to removably interlock with an attachment pillar having a corresponding at least one of a protrusion and a recess.

In an embodiment, the removable denture further comprises an attachment bar permanently embedded within the denture body, the attachment bar comprising a plurality of dental prosthesis attachment sleeves embedded therein. The outer surfaces of the dental prosthesis sleeves can comprise outwardly extending pillar base abutment flanges abutting against dental implant portions including the attachment pillars when the attachment pillars are engaged in the dental prosthesis sleeves.

In an embodiment, the denture body is acrylic-based.

According to a further general aspect, a patient-specific dental prosthesis attachment system for engaging a dental prosthesis to a patient's dental implant, the dental prosthesis attachment system comprising: an implant abutment having a body with a base portion extending along a base portion axis, a head portion extending along a head portion axis, and an attachment pillar protruding from the head portion and extending along the head portion axis at an oblique angle with respect to the base portion axis, the base portion being securable to the dental implant, and the attachment pillar being engageable with the dental prosthesis.

According to another general aspect, a method for designing patient-specific implant abutments for securing to a patient's dental implants. The method comprises the steps of: obtaining a model of a patient's mouth including the dental implants; determining an implant orientation for each one of the patient's dental implants; determining a correction orientation for each one of the dental implants, the correction orientation corresponding to a difference between the implant orientation and an aligned orientation of each one of the dental implants, the aligned orientation being an orientation at which the dental implants extend substantially parallel to one another; and designing an implant abutment for each one of the dental implants, each one of the implant abutment comprising a body with a base portion extending along a base portion axis and a head portion extending along a head portion axis, the base portion being securable to the respective one of the dental implants, wherein, for each one of the implant abutments, an angle between the head portion axis and the base portion axis corresponds to a respective one of the correction orientations.

Other objects, advantages and features of the present invention will become more apparent upon reading of the following non-restrictive description of embodiments thereof, given for the purpose of exemplification only, with reference to the accompanying drawings.

BRIEF DESCRIPTION OF THE DRAWINGS

It will be noted that throughout the appended drawings, like features are identified by like reference numerals.

DETAILED DESCRIPTION

In the following description, the same numerical references refer to similar elements. The embodiments, geometrical configurations, materials mentioned and/or dimensions shown in the figures or described in the present description are embodiments only, given for exemplification purposes only.

Figure 1:
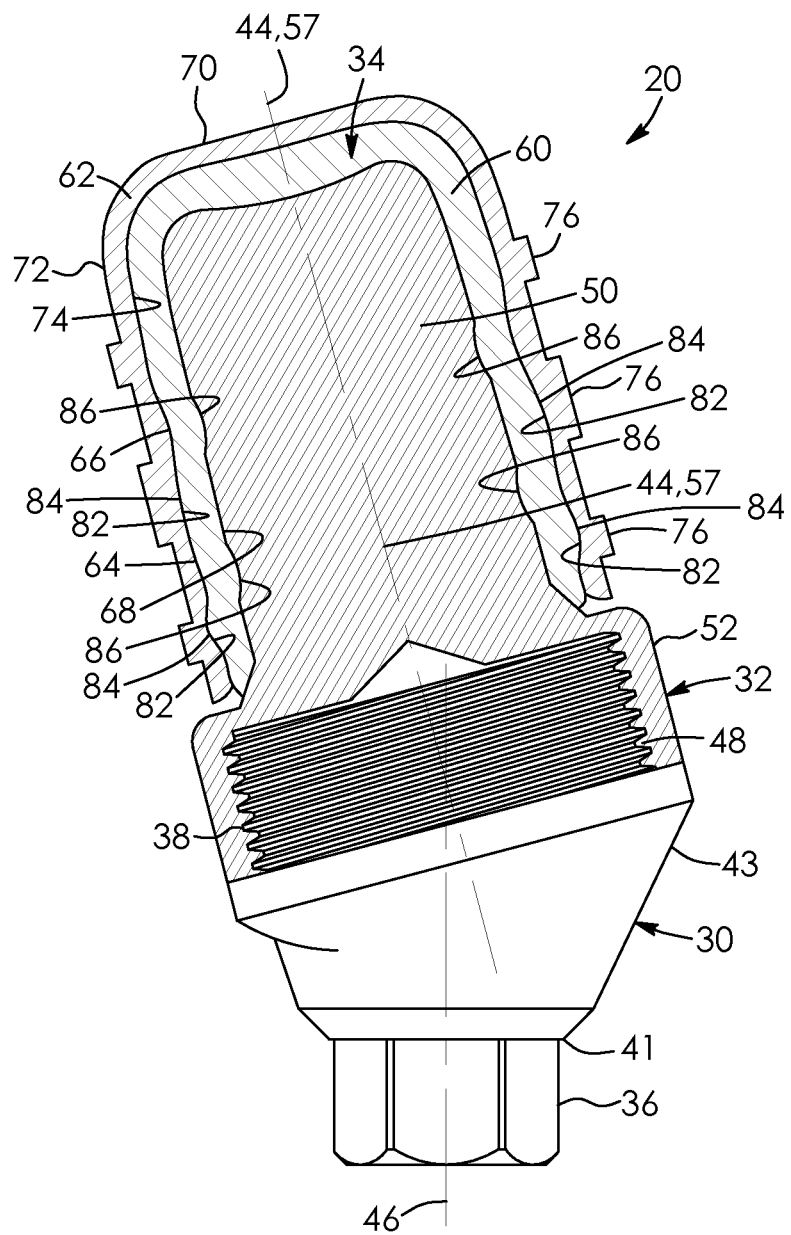
FIG. 1 is a front elevation view, partly sectioned, of a prosthesis attachment system in accordance with an embodiment.
Figure 3:
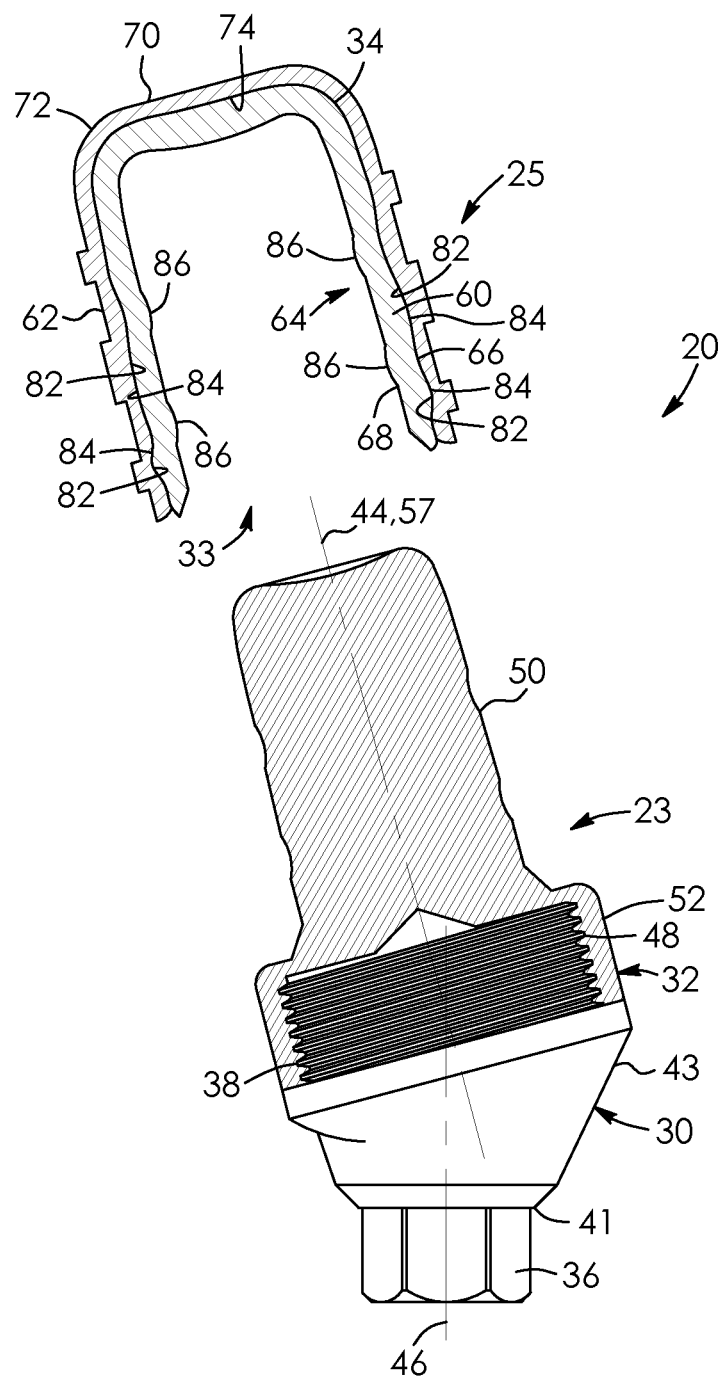
FIG. 3 is a front elevation view, partly sectioned and expanded, of the prosthesis attachment system of FIG. 1, wherein the prosthesis attachment system is separated in a dental implant portion and a dental prosthesis portion.

Referring now to the drawings and, more particularly, referring to FIGS. 1 and 3, there is shown a dental prosthesis attachment system 20 (or dental prosthesis retainer system) in accordance with an embodiment.

Figure 16:
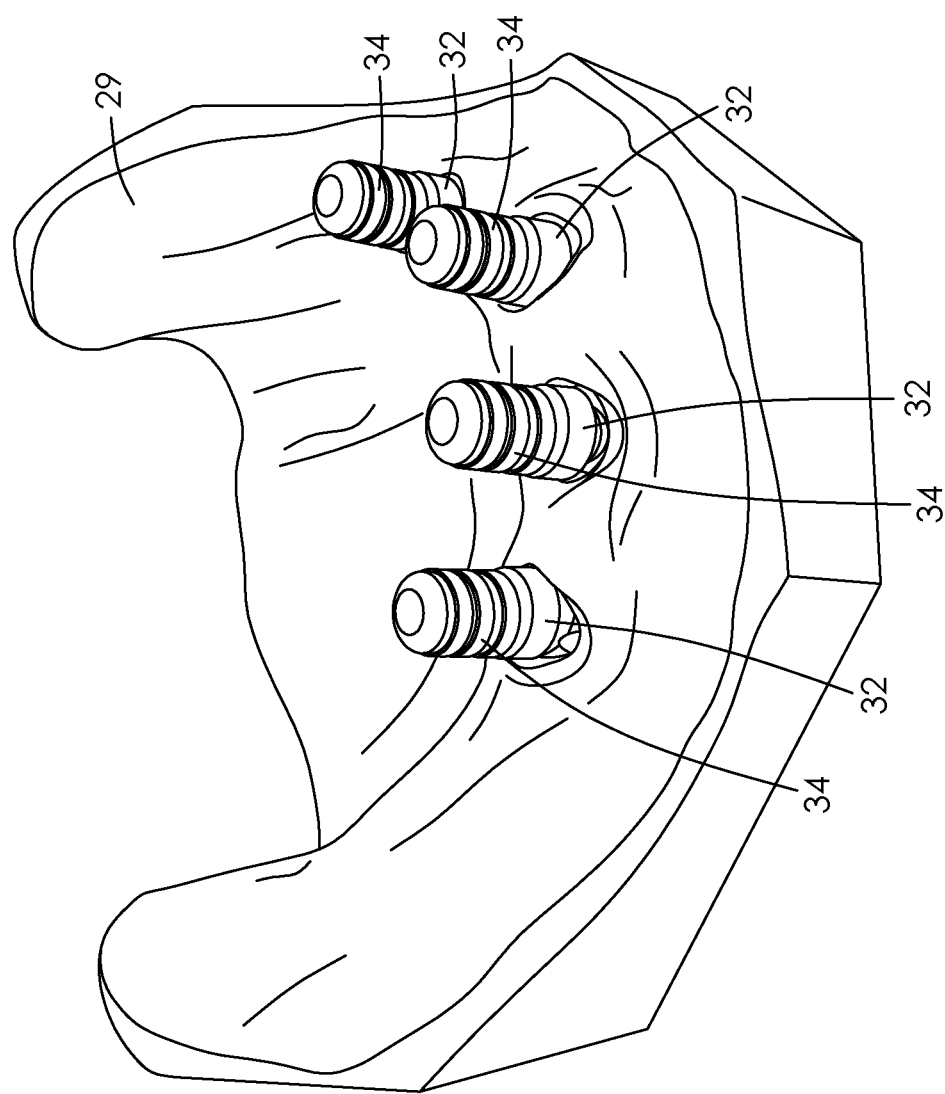
FIG. 16 is a perspective view of the jaw model shown in FIG. 13, wherein the open-ended dental prosthesis sleeve, shown in FIG. 15, is engaged over each one of the dental implant portions in accordance with an embodiment.

The dental prosthesis attachment system 20 can be provided as a kit including a dental implant portion 23 securable to a dental implant 22 (FIG. 4) and a dental prosthesis portion 25 securable to a dental prosthesis 24 (FIGS. 16 and 18), such as a removable denture.

Figure 4:
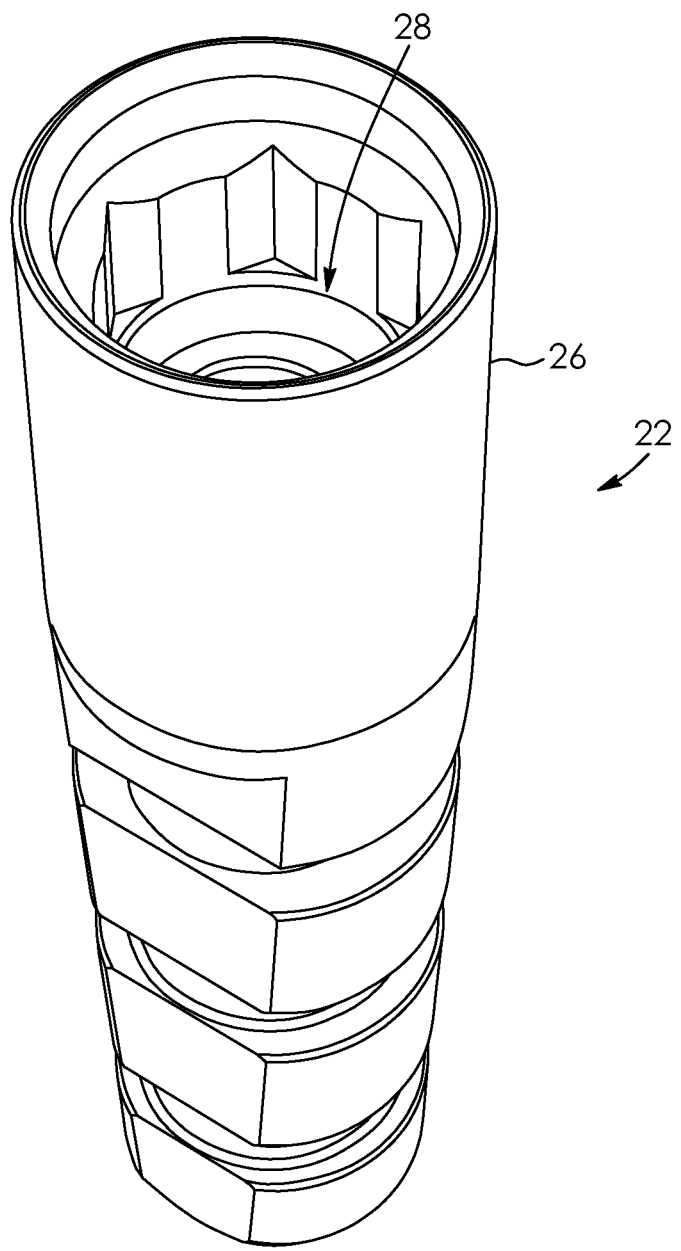
FIG. 4 is a perspective view of a dental implant in accordance with an embodiment.
Figure 5:
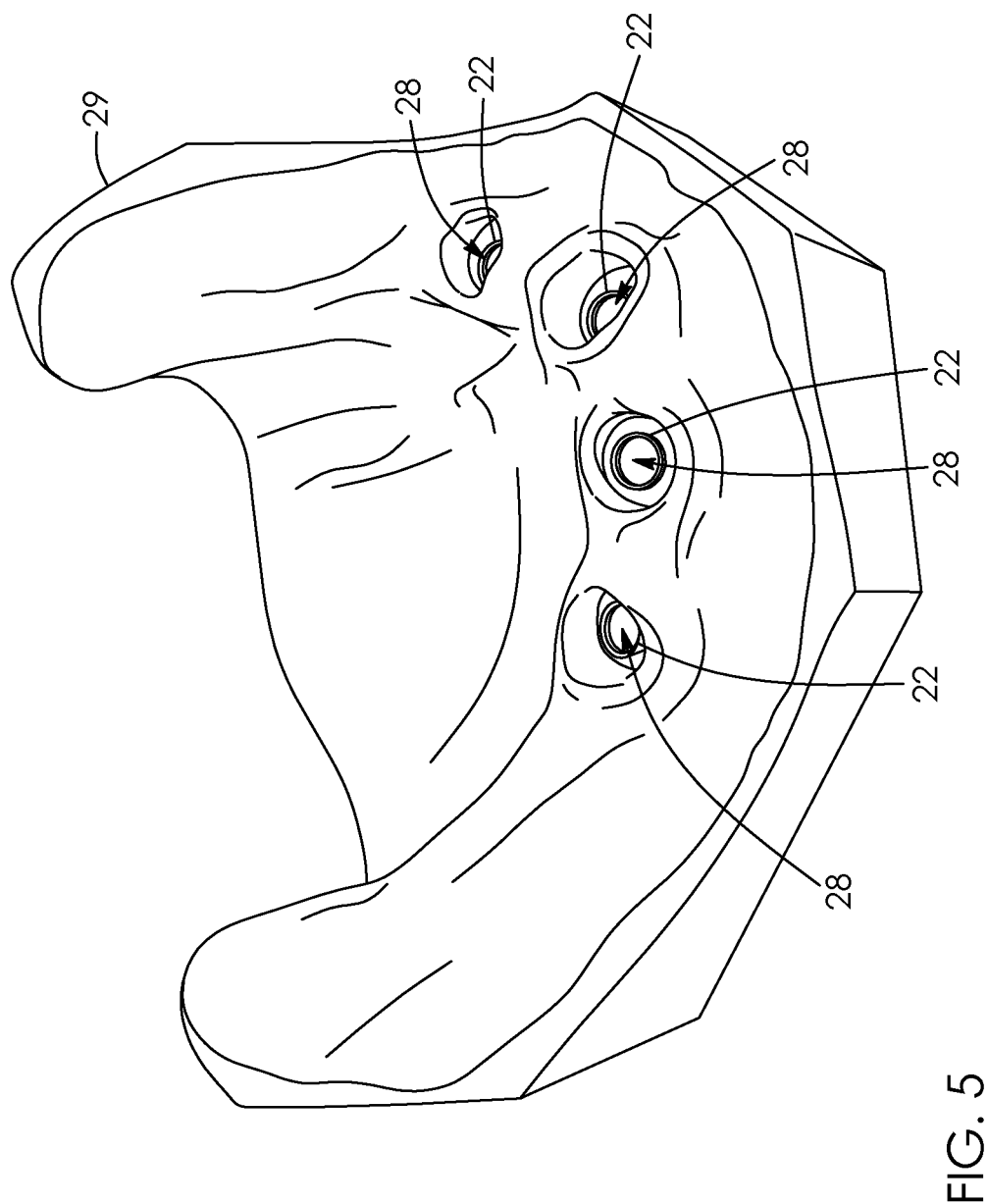
FIG. 5 is a perspective view of four of the dental implants of FIG. 4, inserted in a toothless jaw model, in accordance with an embodiment.

Referring now to FIGS. 4 and 5, it is shown that the dental implant 22 can be a conventional dental implant, such as an endosseous dental implant, extending within a jaw bone and accessible through a gum tissue covering the jaw bone. The dental implant 22 is typically permanently fixed to the jaw bone. In the embodiment shown, the dental implant 22 has a head portion 26 with a cavity 28 defined therein. A head section of an inner peripheral wall of the cavity 28 is hexagonally shaped and another inner section of the inner peripheral wall of the cavity 28 is threaded, the purpose of which will be described in more detail below. It is appreciated that the shape of the dental implant 22 can differ from the embodiment described above and shown in the accompanying drawings.

In the embodiment shown in FIG. 5, four dental implants 22, spaced-apart from one another, are inserted and secured to a model of a jaw 29 for illustrative purposes. When implanting the dental implants 22 in a patient's mouth, the dental implants 22 are inserted in the jaw bone of the patient, as it is known in the art.

Referring back to FIGS. 1 and 3, it is shown that the dental implant portion 23 of the dental prosthesis attachment system 20 comprises an implant abutment 30 which is securable to the dental implant 22 and is configured to pass through the gum tissue when secured to the dental implant. The dental implant portion 23 of the dental prosthesis attachment system 20 further comprises a dental prosthesis engagement section 32. In the embodiment shown, the dental prosthesis engagement section 32 and the implant abutment 30 are two components detachably engageable together. However, in an alternative embodiment, the dental prosthesis engagement section 32 and the implant abutment 30 can be single piece, i.e. provided as a single piece with the dental prosthesis engagement section extending from a head section of the implant abutment 30.

Figure 18:
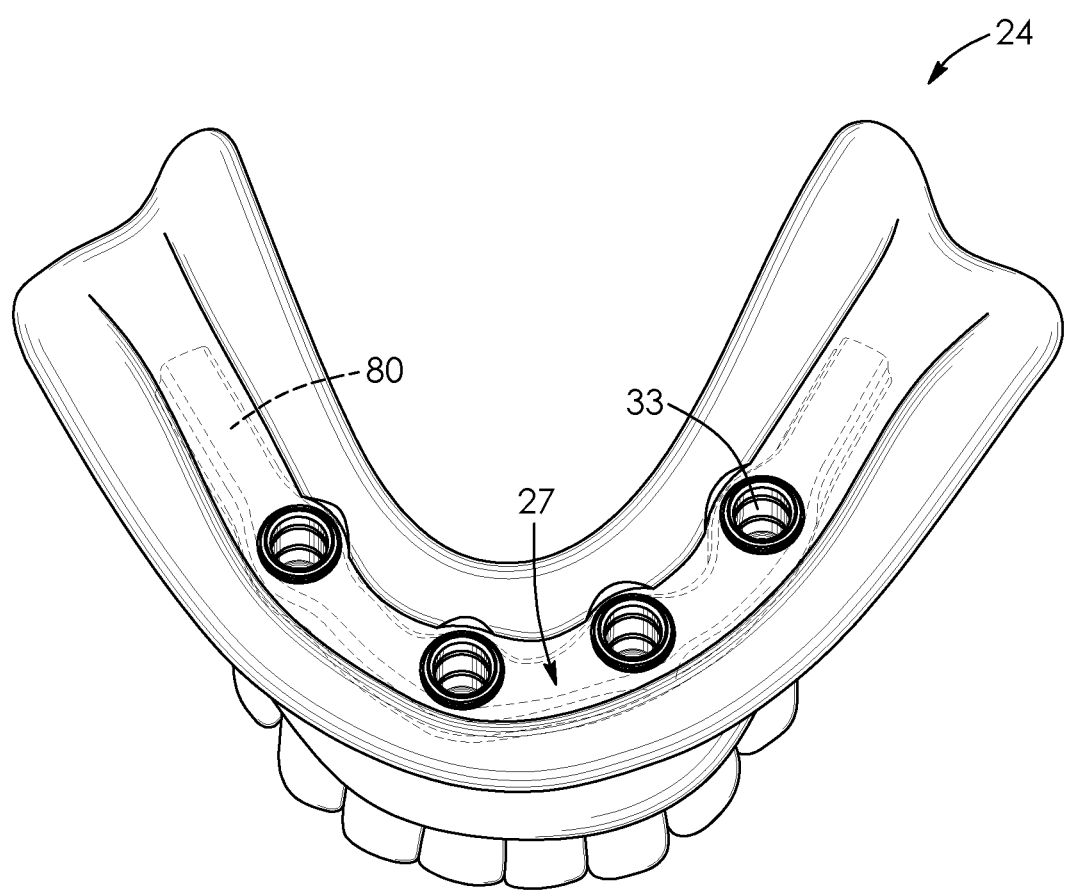
FIG. 18 is a perspective view of a dental prosthesis, according to an embodiment.

The dental prosthesis portion 25 of the dental prosthesis attachment system 20 comprises an open-ended dental prosthesis sleeve 34 which is securable to the dental prosthesis. For instance, for a removable denture, the denture comprises a denture body, typically an acrylic-based body, defining a gum receiving cavity 27 (FIG. 18). The dental prosthesis sleeve 34 is housed in the denture body with the open end opened in the gum receiving cavity 27. Thus, a cavity 33 of the dental prosthesis sleeve 34 is accessible from outside. In an embodiment, as will be described in more detail below, the dental prosthesis can comprise a dental prosthesis bar or an openwork structure connecting together a plurality of open-ended dental prosthesis sleeves 34. The acrylic-based body can surround the dental prosthesis bar and the open-ended dental prosthesis sleeves 34, with the cavities of the open-ended dental prosthesis sleeves 34 being open in the gum receiving cavity 27 and accessible from outside.

The dental implant portion 23 and the dental prosthesis portion 25 of the dental prosthesis attachment system 20 are detachably engageable together to removably connect the dental prosthesis to the dental implant 22.

It should be appreciated that a dental prosthesis can include several kits of the dental prosthesis attachment system 20. For brevity, only one will be described below.

Figure 6:
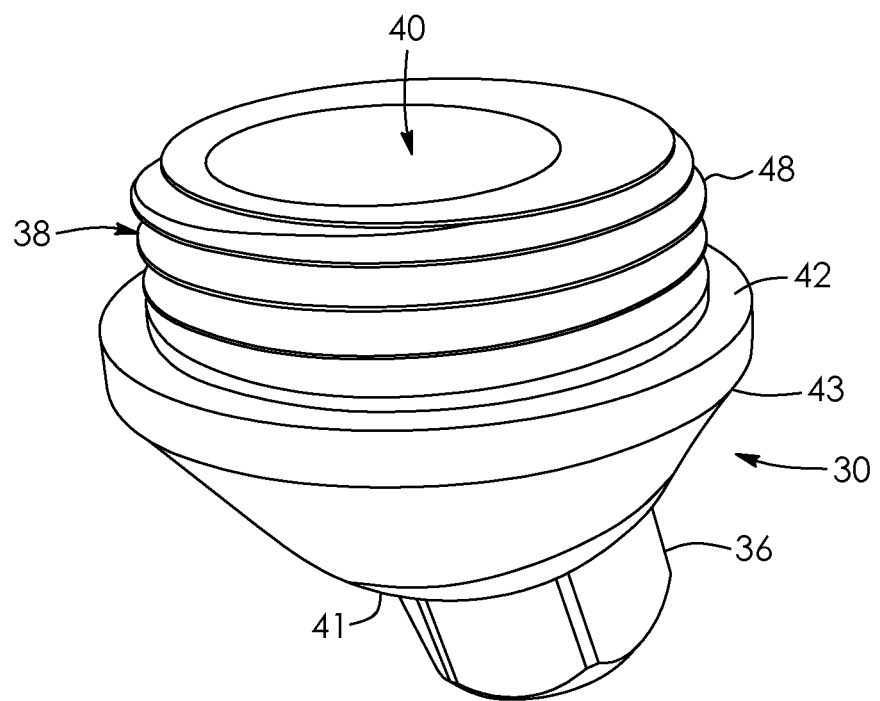
FIG. 6 is a perspective view of an implant abutment in accordance with an embodiment.

As mentioned above, the implant abutment 30 of the dental implant portion is securable to the dental implant 22. In the embodiment shown in FIGS. 6 to 8, the implant abutment 30 includes a body with a base portion 36, a head portion 38, and an intermediate portion 43 extending between the base portion 36 and the head portion 38. The intermediate portion 43 serves to modify the respective orientation of the head portion 38 and base portion 36, as will be described in more detail below. In the embodiment shown, the base portion 36 has a hexagonal outer shape, which is complementary to the shape of the upper portion of the cavity 28 of the dental implant 22 in which the base portion 36 is insertable. The head portion 38 and the intermediate portion 43 extend above the dental implant 22 when the implant abutment 30 and the dental implant 22 are engaged together.

The implant abutment 30 also includes an open-ended channel 40 extending therethrough. Thus, to secure the implant abutment 30 to the dental implant 22, the base portion 36 is inserted in the cavity 28 of the dental implant 22 and a screw (not shown), or any other suitable fastener, is inserted in the open-ended channel 40 and the cavity 28 of the dental implant 22 to secure both components together. The screw engages a threaded section of the inner peripheral wall of the cavity 28 of the dental implant 22. The screw can also engage a threaded section 49 in the open-ended channel 40 of the implant abutment 30.

The complementary shapes of the base portion 36 and the upper portion of the cavity 28 prevent the implant abutment 30 from rotating with respect to the dental implant 22 when securing the two components together. The complementary shapes of the base portion 36 and the upper portion of the cavity 28 can vary from the hexagonal shape shown in the accompanying drawings, provided that relative rotation is prevented when the two are engaged together. The complementary shapes ensure that the implant abutment 30 remains in the predetermined orientation, i.e. the orientation in which the implant abutment 30 is engaged with the dental implant 22 when the two are secured together. It should be appreciated that, in an alternate embodiment, the implant abutment 30 can be secured to the dental implant 22 by any other suitable mechanical fastener(s).

The head portion 38 of the implant abutment 30 is substantially cylindrical in shape, with a peripheral wall section 48 thereof being threaded. The intermediate portion 43 is substantially frusto-conically shaped and extends between the base portion 36 and the head portion 38. It should be appreciated that the shape of the intermediate portion can vary from the embodiment shown. For instance, the shape of the intermediate portion 43 can be designed to substantially conform to the gum tissue anatomy. In the embodiment shown, a length of the peripheral wall of the intermediate portion 43 varies along its perimeter to modify the alignment of the head portion 38, as will be described in more detail below. The implant abutment 30 further comprises an implant abutment flange 41, defined at a junction of the base portion 36 and the intermediate portion 43. The implant abutment flange 41 extends radially from an inner edge of the base portion 36, and serves to abut the dental implant 22 when the implant abutment 30 is secured thereto. The implant abutment 30 also includes a pillar abutment flange 42 spaced-apart from the implant abutment flange 41. The pillar abutment flange 42 is defined at a junction of the head portion 38 and the intermediate portion 43. The head portion 38 extends from the pillar abutment flange 42. The pillar abutment flange 42 defines a seat for the dental prosthesis engagement section 32, as will be described in more detail below. In the embodiment shown, the pillar abutment flange 42 is at an oblique angle, i.e. an angle that is not a right angle or a multiple of a right angle, relative to the implant abutment flange 41. In other words, as shown in FIGS. 1 and 3, a head portion axis 44 extends centrally in the head portion 38, and a base axis 46, extends centrally in the base portion 36. The head portion axis 44 is at an oblique angle relative to the base axis 46. The purpose of the described configuration will be described in more detail below.

Figure 9:
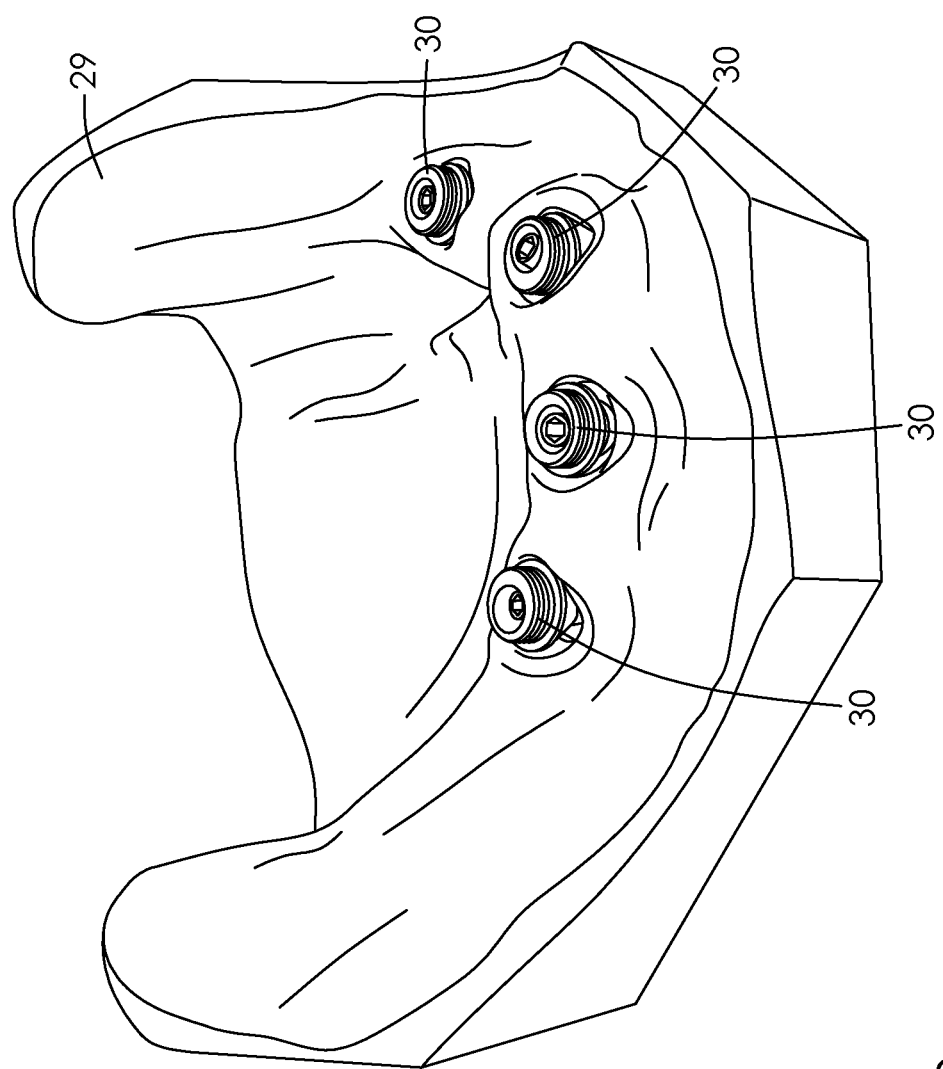
FIG. 9 is a perspective view of the jaw model shown in FIG. 5, wherein the implant abutment, shown in FIG. 6, is secured to each one of the dental implants in accordance with an embodiment.

FIG. 9 shows four implant abutments 30, each one being engaged with a respective one of the dental implants 22 inserted and secured to the jaw model 29, which is used to represent a patient's jaw. The head portions 38 extend outwardly from the jaw bone and extend substantially parallel to one another, as will be described in more detail below.

Figure 10:
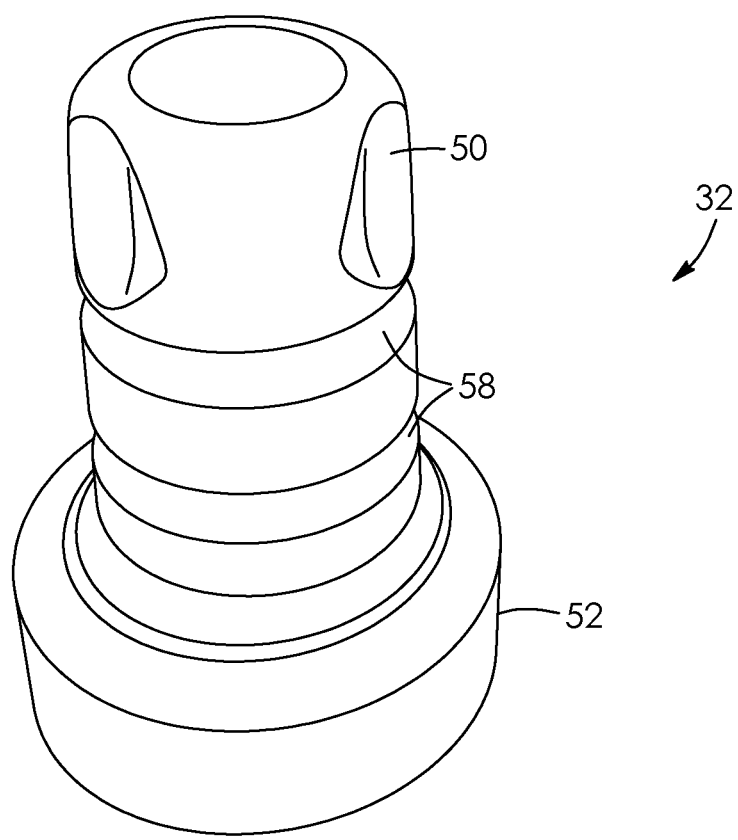
FIG. 10 is a perspective view of a dental prosthesis engagement section in accordance with an embodiment.
Figure 11:
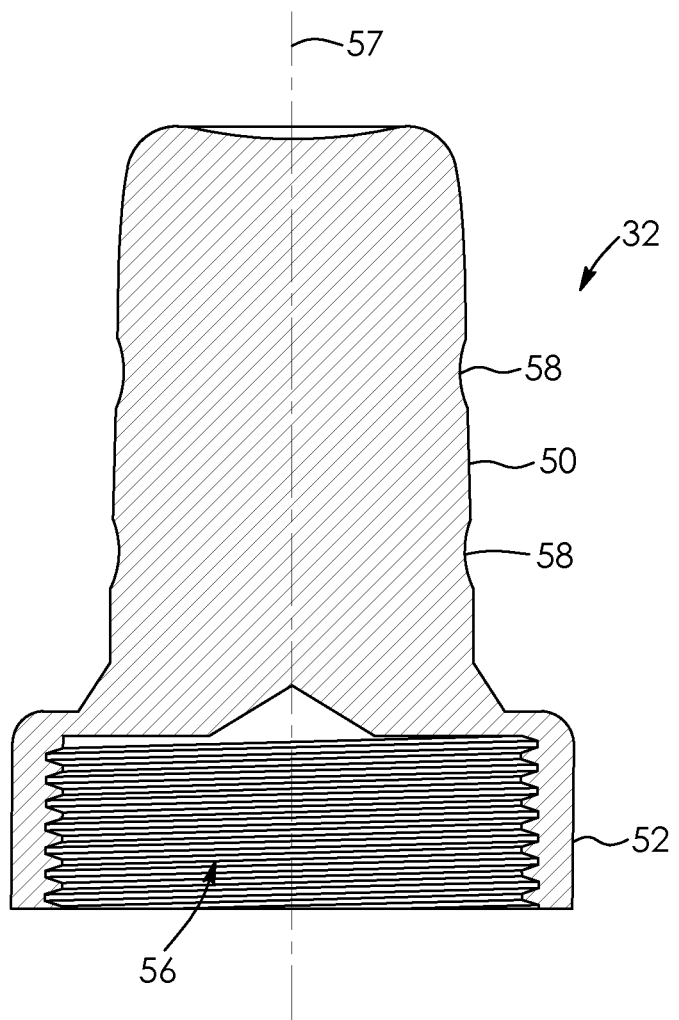
FIG. 11 is a sectional view of the dental prosthesis engagement section of FIG. 10.
Figure 12:
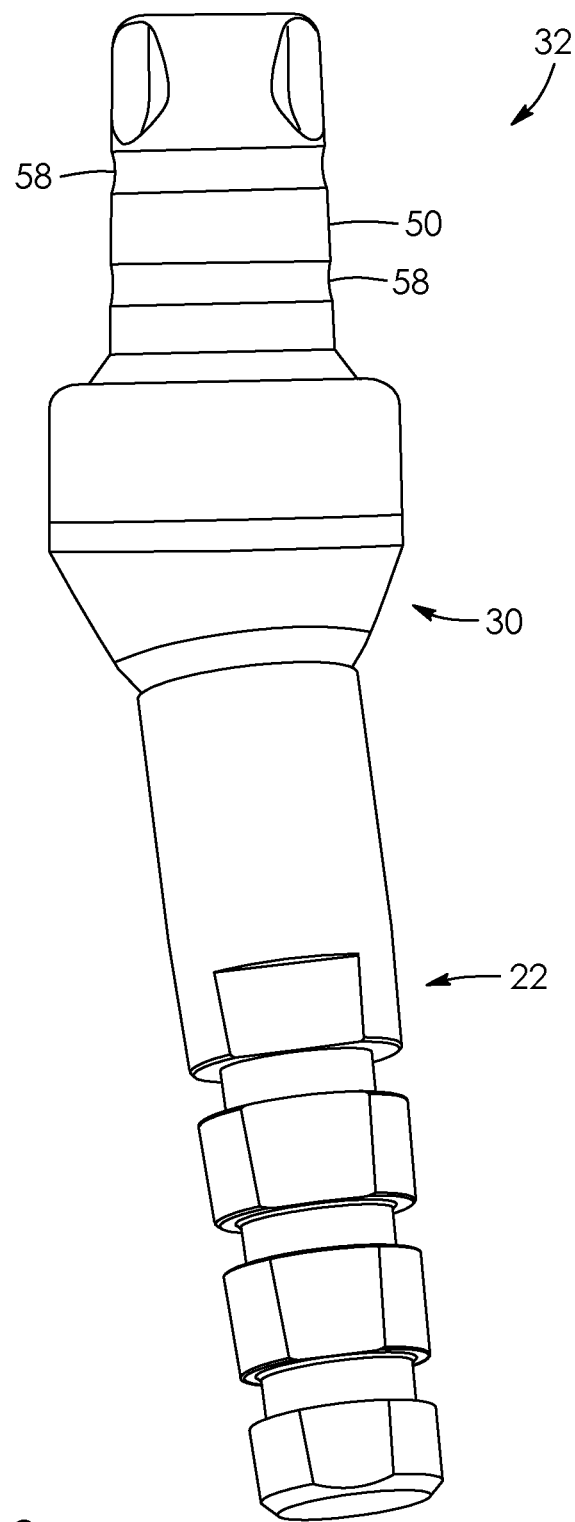
FIG. 12 is a perspective view of the dental prosthesis engagement section of FIG. 10 secured to the implant abutment shown in FIG. 6 in accordance with an embodiment.

Referring now to FIGS. 10 to 12, it is shown that the dental prosthesis engagement section 32 comprises an attachment pillar 50 and a base portion 52. In the embodiment shown, both the attachment pillar 50 and the base portion 52 are substantially circular in shape and are concentric. The base portion 52 of the dental prosthesis engagement section 32 comprises a cavity 56 defined therein with an open end. The inner peripheral wall of the cavity 56 is threaded, thus allowing the dental prosthesis engagement section 32 to be detachably secured to the implant abutment 30 by screwing its base portion 52 to the head portion 38. An outer peripheral wall of the attachment pillar 50 comprises two spaced-apart peripheral recesses 58 (or grooves), the purpose of which will be described in more detail below. The peripheral recesses 58 contour the attachment pillar 50. When the dental prosthesis engagement section 32 is secured to the implant abutment 30, the base portion 52 abuts the pillar abutment flange 42. A central axis 57 (shown in FIGS. 1 and 3) of the dental prosthesis engagement section 32 is aligned with the head portion axis 44.

Figure 13:
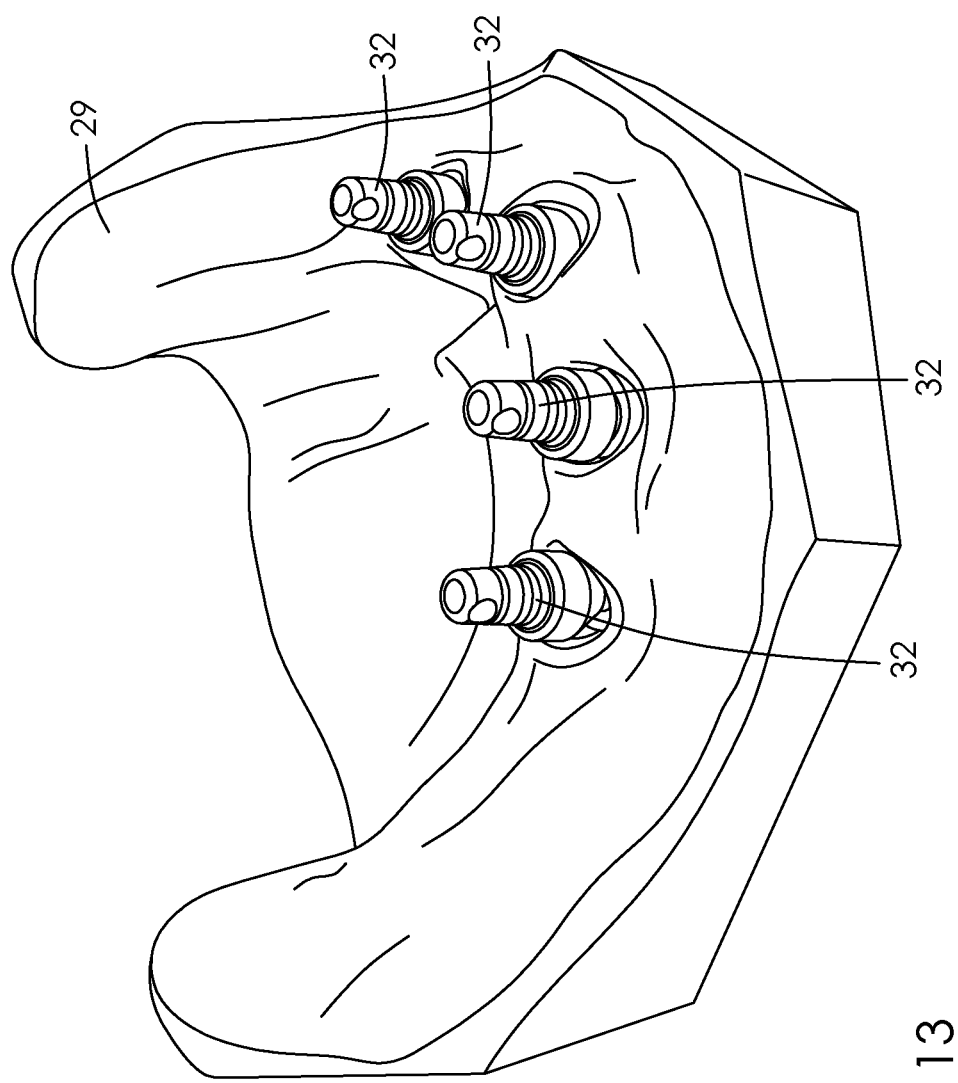
FIG. 13 is a perspective view of the jaw model, shown in FIG. 9, wherein the dental prosthesis engagement section, shown in FIG. 10, is secured to each one of the implant abutments to define four dental implant portions of the dental prosthesis attachment system in accordance with an embodiment.
Figure 14:
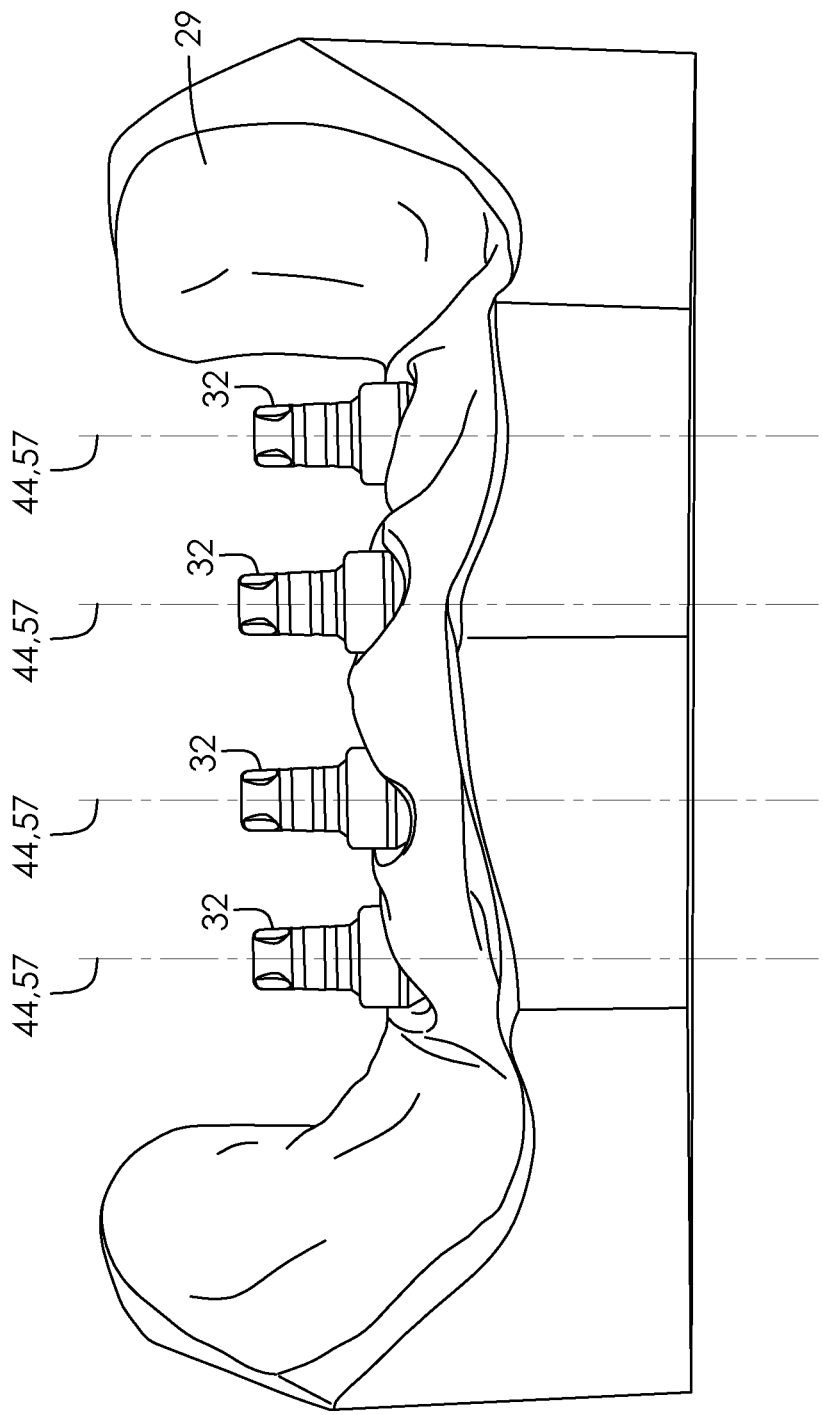
FIG. 14 is a front elevation view of the jaw model including the four dental implant portions shown in FIG. 13.

FIGS. 13 and 14 show four dental prosthesis engagement sections 32, each one being engaged with a respective one of the implant abutments 30, which are themselves engaged with the dental implants 22 inserted and secured to the jaw model 29. Just like the head portions 38 of the implant abutments 30, the attachment pillars 50 extend outwardly from the jaw bone. The head portions 38 and the attachment pillars 50 extend substantially parallel to one another, since their axes 44, 57 are parallel.

As mentioned above, and with reference to FIGS. 1, 3, 15 and 16, the dental prosthesis portion 25 of the dental prosthesis attachment system 20 comprises the open-ended dental prosthesis sleeve 34 which is securable to the dental prosthesis. In the embodiment shown, the open-ended dental prosthesis sleeve 34 comprises two components: a retention sleeve 60 made of resilient material and a rigid sleeve 62 which defines a housing, the rigid sleeve 62 being made of a substantially rigid material such as suitable metals, alloys, and ceramics. The retention sleeve 60 can be made of a synthetic polymer such as, and without being limited to, nylon and polyethylene. In an embodiment, the retention sleeve 60 is made of a resilient material such that it can conform to an interface between the attachment pillar 50 and the sleeve 34. In an embodiment, the retention sleeve 60 is a nylon retention sleeve. The retention sleeve 60 and the rigid sleeve 62 have substantially the same shape with the retention sleeve 60 being inserted in the rigid sleeve 62. Both sleeves 60, 62 have a closed end and an open-ended end and are housed in the denture body with the open-ended end opened in the gum receiving cavity 27. The retention sleeve 60 comprises a peripheral wall 64 with an outer surface 66 and an inner surface 68. Similarly, the rigid sleeve 62 comprises a peripheral wall 70 with an outer surface 72 and an inner surface 74. The outer surface 66 of the retention sleeve 60 is superposed to the inner surface 74 of the rigid sleeve 62, and the two are secured together. Once secured together, the retention sleeve 60 cannot be disengaged from the rigid sleeve 62. The outer surface 72 of the rigid sleeve 62 is in contact with the denture body, or any other dental prosthesis, as will be described in more detail below. In an embodiment, the retention sleeve 60 conforms to the inner surface 74 of the rigid sleeve, and an outer peripheral wall of the attachment pillar 50 when the two are engaged, thereby removably interlocking the two components.

In the embodiment shown, the outer surface 72 of the rigid sleeve 62 comprises three spaced-apart peripheral protrusions 76, contouring the rigid sleeve 62. The protrusions 76 increase the contact (interference) surface between the rigid sleeve 62 and the dental prosthesis, thereby increasing the mechanical retention. The protrusions 76 increase the cohesion between the rigid sleeve 62 and the body of the dental prosthesis surrounding the rigid sleeve 62 and mechanically retain the rigid sleeve 62 which is in the body of the dental prosthesis. The inner surface 74 of the rigid sleeve 62 includes spaced-apart peripheral recesses 82. In the embodiment shown, each one of the peripheral recesses 82 is aligned with a respective one of the peripheral protrusions 76; however, in an alternate embodiment, they can be misaligned. The outer surface 66 of the retention sleeve 60 comprises spaced-apart peripheral protrusions 84, contouring the retention sleeve 60. Each one of the peripheral protrusions 84 is complementary in shape to a respective one of the peripheral recesses 82 of the rigid sleeve 62 and is aligned and engaged therein when the retention sleeve 60 is housed in the rigid sleeve 62 in an engaged configuration. The complementary peripheral protrusions 84 and peripheral recesses 82 increase the retention of the retention sleeve 60 within the rigid sleeve 62. Finally, the inner surface 68 of the retention sleeve 60 comprises two spaced-apart peripheral protrusions 86. Each one of the peripheral protrusions 86 is complementary in shape to a respective one of the peripheral recesses 58 of the attachment pillar 50 and is aligned and engaged therewith when the attachment pillar 50 is housed in the open-ended dental prosthesis sleeve 34 in an engaged configuration. The complementary peripheral protrusions 86 and peripheral recesses 58 increase the retention of the attachment pillar 50 within the dental prosthesis sleeve 34, and thus the engagement of the dental prosthesis with the dental implant 22.

Thus, the complementary peripheral recesses and protrusions provided on the attachment pillar 50, the retention sleeve 60, and the rigid sleeve 62 increase the interference surface and thereby the retention of the dental prosthesis on the dental implant 22. Thus, the dental prosthesis can support higher pressure without undesired detachment.

It should be appreciated that one or several of the recesses and protrusions of the embodiment described above can be inverted provided that two engageable or interlockable components are provided with complementary male and female members. Furthermore, the number, the configuration, and the shape (including their depth and length) of the recesses and protrusions can differ from the embodiment described above.

Figure 15:
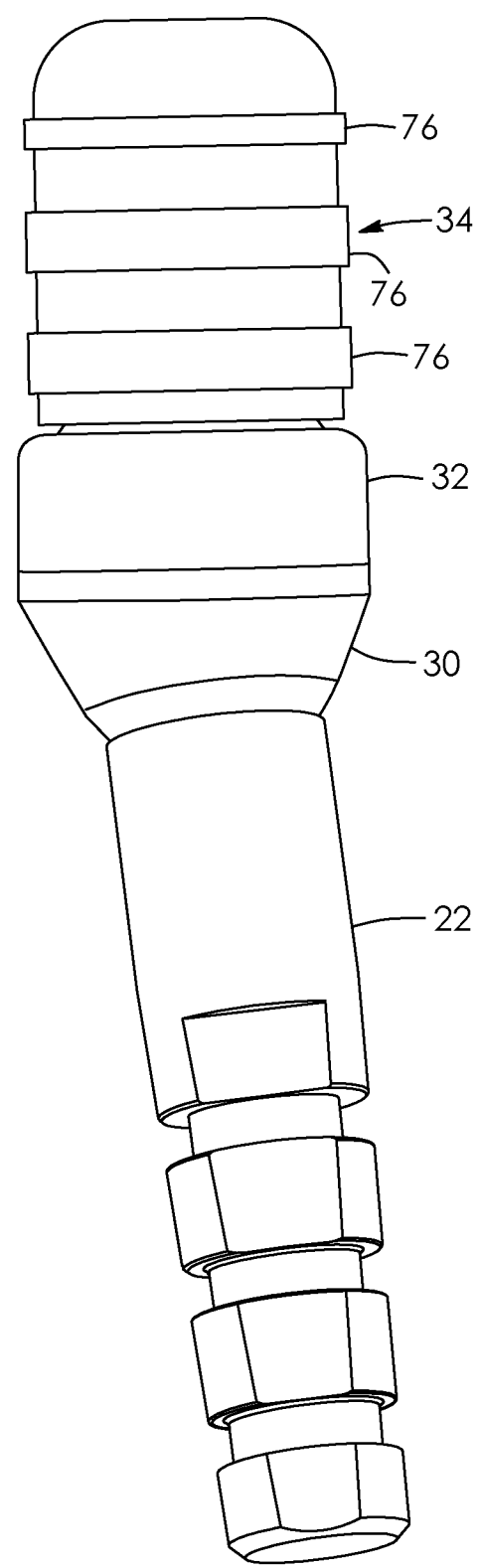
FIG. 15 is a perspective view of an open-ended dental prosthesis sleeve engaged over the dental implant portion shown in FIG. 12.

As described above, in the embodiment shown, the pillar abutment flange 42 is at an oblique angle relative to the implant abutment flange 41, allowing the adjustment of the angle of the attachment pillar 50. As mentioned above, a dental prosthesis, such as a removable denture, can include a plurality of dental prosthesis portions 25, each one being engageable with a respective attachment pillar 50. For a dental prosthesis which includes several open-ended dental prosthesis sleeves, it is easier to engage the dental prosthesis 24 when the attachment pillars 50 extend in a substantially parallel configuration, as shown in FIGS. 14 and 15. However, in some implementations, it is possible that the dental implants 22 to which the attachment pillars 50 are engaged do not extend parallel to one another. In the present configuration, it is possible to adjust the orientation of one or several of the attachment pillars 50 in a manner such that they extend substantially parallel to one another. This allows for the head portion axes 44 of the attachment pillars to extend substantially parallel to one another.

Figure 7:
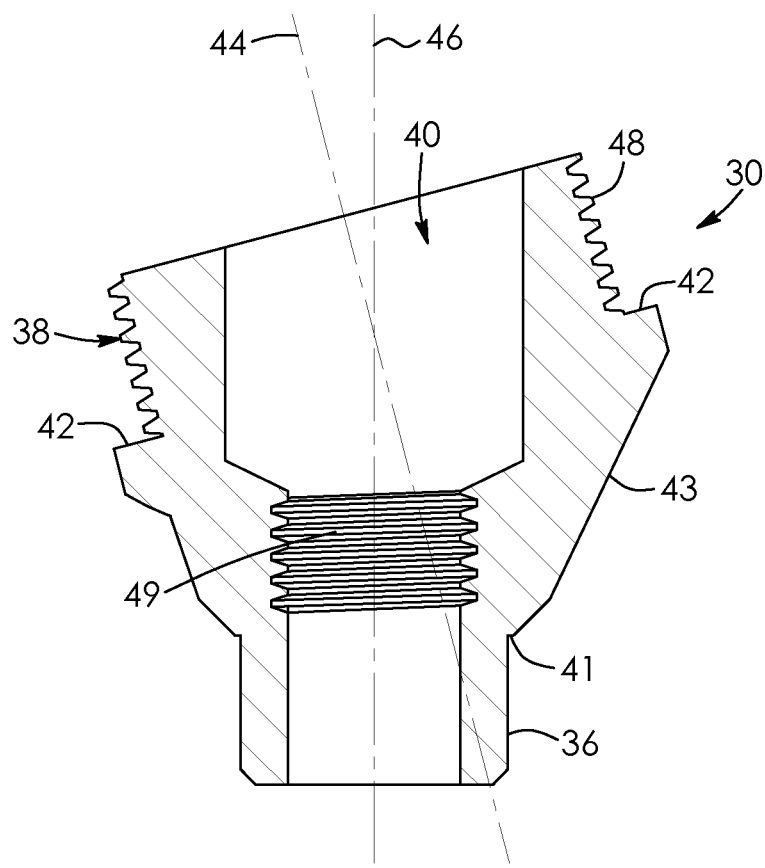
FIG. 7 is a sectional view of the implant abutment of FIG. 6.
Figure 8:
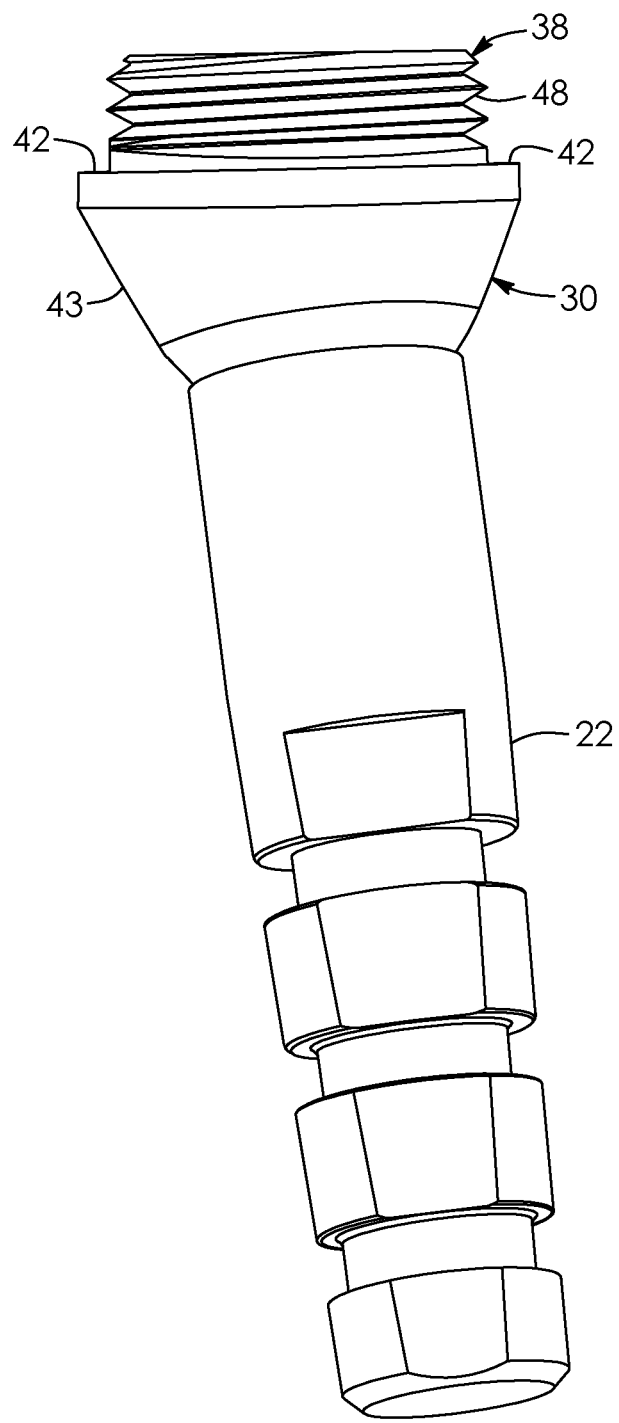
FIG. 8 is a perspective view of the implant abutment of FIG. 6 secured to the dental implant of FIG. 4.

Accordingly, the described embodiment allows correcting the orientation of a dental implant if the dental implant is not aligned with other implants, or if it would cause an attachment pillar extending therefrom to not line up properly with a corresponding dental prosthesis engagement section. According to the described embodiment, customized patient-specific implant abutments 30 can be designed and fabricated in order to make it easier to engage a dental prosthesis 24 with attachment pillars 50. The customized implant abutments 30 can be designed by first obtaining a model of a patient's mouth and, more particularly, the jaw including dental implants 22, such as the one illustrated in FIG. 5. The model can be a virtual model obtained, for example, by scanning the patient's mouth, or a physical model. Next, using the virtual or physical model, the implant positions and orientations of the patient's dental implants 22 can be determined. Using the implant orientations, a desirable correction orientation of the dental implants 22 can be determined. The correction orientation should correspond to an orientation of the dental implants 22 where attachment pillars 50 extending therefrom are parallel to one another, as shown in FIG. 14, to be easily insertable in the dental prosthesis sleeves 34 of the dental prosthesis 24. For each one of the dental implants 22, a correction orientation can be determined by subtracting the actual orientation of the implant with the desirable or aligned orientation of that implant. Once a correction orientation is determined, an implant abutment 30 can be designed and fabricated as shown in FIG. 7, such that an oblique angle between the head portion axis 44 and the base portion axis 46 corresponds to the correction orientation. When the customized implant abutment 30 is secured to its respective implant, the angle of the attachment pillar 50 will be realigned with respect to the implant 22 by the correction orientation. As a result, the attachment pillar 50 can extend from the implant abutment 30 at the aligned orientation, and thus be aligned with (or extend substantially parallel to) other attachment pillars 50 as shown in FIG. 14.

Figure 17:
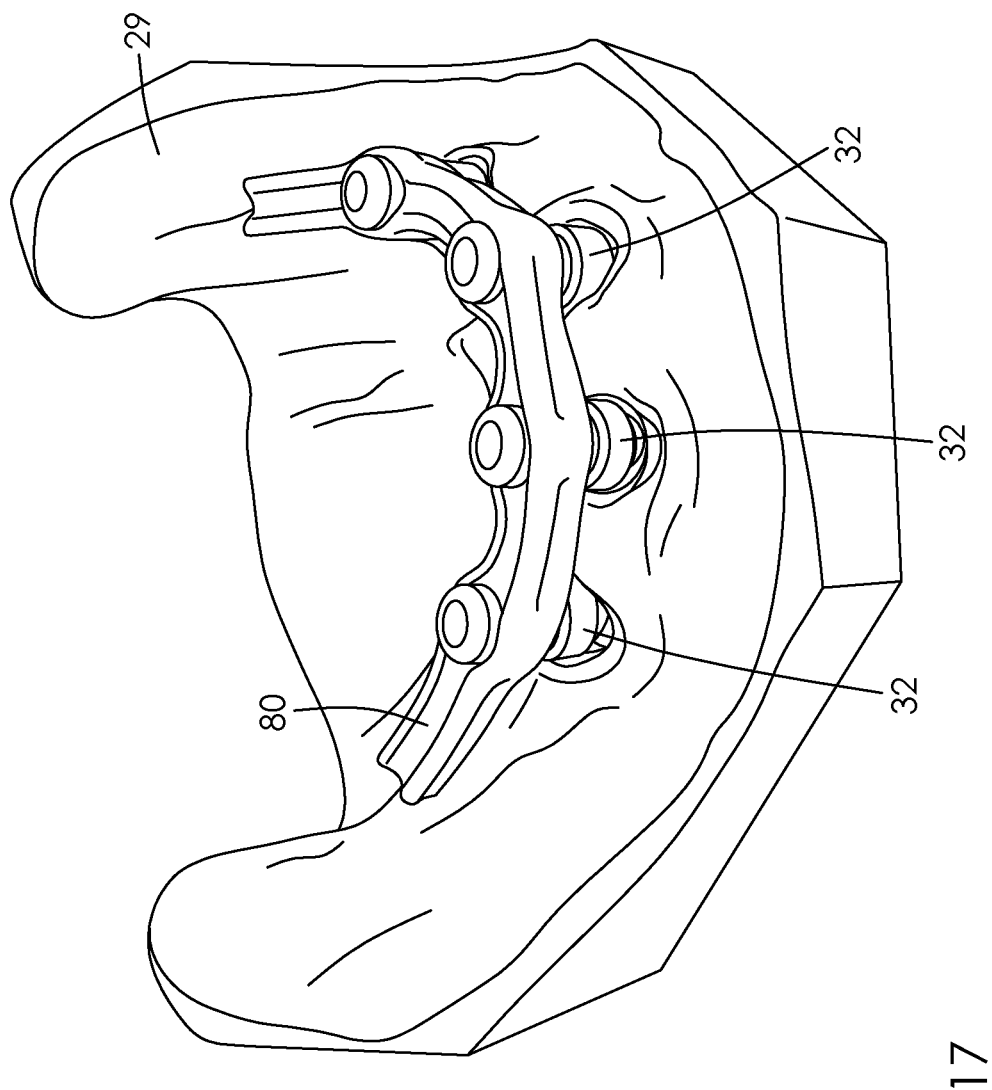
FIG. 17 is a perspective view of the jaw model shown in FIG. 16, wherein a component of a dental prosthesis is engaged with the four dental implant portions with the dental prosthesis housing four open-ended dental prosthesis sleeves shown in FIG. 15 in accordance with an embodiment.

Referring now to FIGS. 17 and 18, there is shown an attachment bar 80 of a dental prosthesis 24. The attachment bar 80 is contained in the dental prosthesis mold when the latter is molded. Thus, the body of the dental prosthesis 24 is molded around the attachment bar 80 and the latter cannot be removed from the dental prosthesis when it is formed. The attachment bar 80 is lodged in the body of the dental prosthesis, which can be, for example, an acrylic-based body. The attachment bar 80 includes a plurality of dental prosthesis portions 25 of the dental prosthesis attachment system 20. In the embodiment shown in FIG. 17, the attachment bar 80 comprises four spaced-apart dental prosthesis portions 25. The dental prosthesis portions 25 can be embedded within or permanently secured to the attachment bar 80, either with an adhesive, with cement, or by friction fit (also known as interference fit), with the cavity 33 of the dental prosthesis sleeve 34 being accessible through a gum-receiving cavity in the dental prosthesis 24. In an alternate embodiment, the attachment bar 80 can be formed from a single piece, along with the rigid sleeve(s) 62 of the dental prosthesis portion 25. For instance, the attachment bar 80 and the rigid sleeve(s) 62 can be molded together or manufactured as a single piece. The dental prosthesis can be engaged with the dental implants by inserting each one of the dental implant portions 23 protruding from the jaw in a respective one of the cavities 33 of the dental prosthesis sleeves 34.

Figure 2:
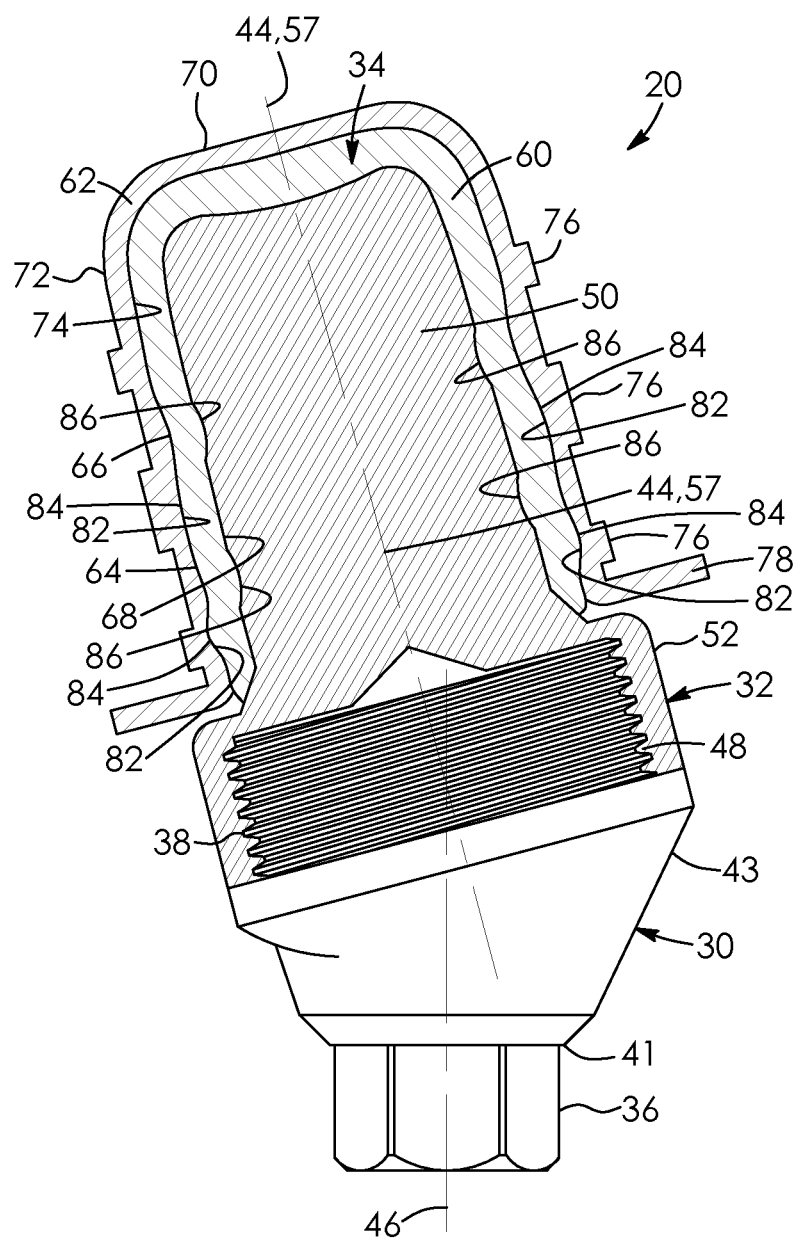
FIG. 2 is a front elevation view, partly sectioned, of a prosthesis attachment system in accordance with an alternate embodiment, wherein a dental prosthesis portion includes a pillar base abutment.

With further reference to FIG. 2, the dental prosthesis sleeve 34 can be provided with a pillar base abutment flange 78 for abutting against the base portion 52 of the dental prosthesis engagement section 32. In the illustrated embodiment, the pillar base abutment 78 is integrally formed as part of the rigid sleeve 62, and is a flange which extends radially outward therefrom. When the attachment pillar 50 is received in the open-ended dental prosthesis sleeve 34, the pillar base abutment flange 78 abuts against the base portion 52 and limits the insertion. For example, when a patient is biting or chewing, significant vertical forces are applied to the dental prosthesis 24, biasing the prosthesis in a downward direction towards the patient's dental implants. In the present configuration, the pillar base abutment flange 78 can counteract these forces by abutting against the base portion 52 of the dental prosthesis engagement section 32.

In an alternate embodiment (not shown), a plurality of dental prosthesis portions 25 can be connected together through an openwork structure (mesh).

Several alternate embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention. The scope of the invention is therefore intended to be limited solely by the scope of the appended claims.

The invention claimed is:

1. A dental prosthesis attachment system comprising:
a removable dental prosthesis having a body defining a gum receiving cavity;
an attachment bar including a plurality of spaced-apart dental prosthesis portions and at least one connecting segment extending between adjacent ones of the dental prosthesis portions, the at least one connecting segment being secured to respective outer surfaces of the adjacent ones of the dental prosthesis portions, the dental prosthesis portions and the at least one connecting segment being permanently embedded within the body of the removable dental prosthesis, the body of the removable dental prosthesis being molded over the at least one connecting segment and the dental prosthesis portions with the at least one connecting segment being surrounded by the body of the removable dental prosthesis, each one of the dental prosthesis portions comprising a prosthesis sleeve open at one end and closed at an opposed end and defining an inner cavity lined with a retention material defining an inner peripheral wall having a closed figure shape having at least one of a protrusion and a recess, the inner cavities of the dental prosthesis sleeves being spaced-apart from one another and having a closed figure shape access port at the open end and opened in the gum receiving cavity of the removable dental prosthesis when the attachment bar is embedded in the body of the removable dental prosthesis; and
a plurality of dental implant portions securable to at least one endosseous dental implant and removably engageable with the dental prosthesis portions, each one of the dental implant portions comprising an attachment pillar removably insertable within the inner cavity of a corresponding one of the dental prosthesis sleeves, the attachment pillar having a peripheral wall provided with at least one of a protrusion and a recess removably interlockable by friction fit with the at least one of the recess and the protrusion on the inner peripheral wall of the inner cavity.

2. The dental prosthesis system according to claim 1, wherein each one of the dental prosthesis portions comprises an outer rigid sleeve and an inner flexible sleeve removably fitted therein, the outer rigid sleeve providing the outer surface of the dental prosthesis portion, and the inner flexible sleeve comprising the retention material and providing the inner peripheral wall of dental prosthesis portion, the outer surface of the dental prosthesis portion being surrounded by the body of the removable dental prosthesis.

3. The dental prosthesis system according to claim 2, wherein the outer rigid sleeve comprises an inner wall and the inner flexible sleeve comprises an outer wall, the inner wall of the outer rigid sleeve being provided with spaced-apart peripheral recesses and the outer wall of the inner flexible sleeve being provided with complementary shaped spaced-apart peripheral protrusions, and the outer surface of the dental prosthesis portion comprises at least one of a recess and a protrusion.

4. The dental prosthesis system according to claim 3, wherein the at least one of the recess and the protrusion on the outer surface of the dental prosthesis portion is aligned with the at least one of the recess and the protrusion on at least one of: the inner wall of the outer rigid sleeve, the outer wall of the inner flexible sleeve and the inner peripheral wall in the inner cavity.

5. The dental prosthesis system according to claim 1, further comprising at least one endosseous implant, an abutment secured to the endosseous dental implant, and a dental prosthesis engagement section removably secured to the implant abutment, the dental prosthesis engagement section comprising a base portion from which the attachment pillar extends, the base portion of the dental prosthesis engagement section being provided with a cavity having an open end fitted over the implant abutment.

6. The dental prosthesis system according to claim 1, wherein an outer surface of the dental prosthesis sleeve comprises an outwardly extending pillar base abutment flange abutting against the dental implant portion when the dental prosthesis sleeve and the dental implant are engaged together.

7. The dental prosthesis system according to claim 1, wherein the inner cavities of the dental prosthesis sleeves extend substantially parallel to one another.

8. The dental prosthesis system according to claim 7, wherein the implant abutment comprises a head portion, a base portion and an intermediate portion extending therebetween, the head portion comprising a pillar abutment flange abutting against the base portion of the dental prosthesis engagement section, and the base portion comprising an implant abutment flange abutting against the endosseous dental implant and at least one of the pillar abutment flanges is obliquely angled relative to the implant abutment flange, thereby positioning the attachment pillar to extend from the base portion of the implant abutment at an oblique angle.

9. A kit for attaching a removable dental prosthesis to an endosseous dental implant, the removable dental prosthesis having a body defining a gum receiving cavity; the kit comprising:
an attachment bar embeddable within the body of the dental prosthesis, the attachment bar comprising a plurality of spaced-apart dental prosthesis portions and at least one connecting segment physically connecting a respective one of the dental prosthesis portions to an adjacent one of the dental prosthesis portions, each one of the dental prosthesis portions comprising a dental prosthesis sleeve open at one end and closed at an opposed end and having an inner cavity lined with a retention material defining an inner peripheral wall having at least one of a protrusion and a recess, the inner cavities of the dental prosthesis sleeves being spaced apart from one another, the body of the removable dental prosthesis being moldable around the at least one connecting segment and the dental prosthesis portions being spaced-apart from one another with a portion of the removable dental prosthesis extending between adjacent ones of the dental prosthesis portions, the inner cavities being accessible through the open end opened in the gum receiving cavity of the removable dental prosthesis and the at least one connecting segment being embedded in the body of the removable dental prosthesis; and a plurality of dental implant portions securable to the endosseous dental implant and removably engageable with each one of the dental prosthesis portions, the dental implant portion comprising an attachment pillar sized and shaped for removably fitting within the inner cavity of a corresponding one of the dental prosthesis sleeves, the attachment pillar having a peripheral wall provided with at least one of a protrusion and a recess removably interlockable by a friction fit with the at least one of the recess and the protrusion on the inner peripheral wall of a corresponding one of the inner cavities.

10. The kit according to claim 9, wherein the dental prosthesis portions have an outer surface surrounded by the body of the removable dental prosthesis.

11. The kit according to claim 9, wherein the inner cavities of the dental prosthesis sleeves extend substantially parallel to one another.

12. A patient-specific dental prosthesis attachment system for engaging a removable dental prosthesis to a patient's dental implant, the dental prosthesis attachment system comprising:

an attachment bar permanently embedded in a body of the dental prosthesis, the attachment bar comprising a plurality of spaced-apart dental prosthesis portions and at least one connecting segment physically connecting a respective one of the dental prosthesis portions to an adjacent one of the dental prosthesis portions, the at least one connecting segment being surrounded by the body of the dental prosthesis, each one of the dental prosthesis portions comprising a dental prosthesis sleeve open at one end and closed at an opposed end, and the dental sleeve comprising an outer rigid sleeve and an inner flexible sleeve removably fitted in the outer rigid sleeve with a closed figure shape access port at the open end opened in a gum receiving cavity of the dental prosthesis body, wherein the dental prosthesis portions extend substantially parallel to one another; and a plurality of implant abutments, each one of the implant abutments having a body with a base portion extending along a base portion axis, a head portion extending along a head portion axis, and an attachment pillar protruding from the head portion and at least one of the attachment pillars extending along the head portion axis at an oblique angle with respect to the base portion axis, the base portion being securable to the patient's dental implant with the head portion axes of the attachment pillars extending substantially parallel to one another when secured to the patient's dental implant, and the attachment pillar being removably engageable by a friction fit with a corresponding one of the dental prosthesis portions through the corresponding one of the dental prosthesis sleeves.

13. The patient-specific dental prosthesis attachment system according to claim 12, wherein the patient's dental implant comprises a plurality of dental implants and each one of the implant abutments is securable to a respective one of the patient's dental implants.

14. The patient-specific dental prosthesis attachment system according to claim 13, wherein the head portion axis extends centrally through the head portion and the base portion axis extends centrally through the base portion of a respective one of the implant abutments.

15. A dental prosthesis system comprising:

a removable dental prosthesis comprising a body defining a gum receiving cavity;

an attachment bar permanently embedded in a body of the dental prosthesis, the attachment bar comprising a plurality of dental prosthesis portions and at least one connecting segment physically connecting a respective one of the dental prosthesis portion to an adjacent one of the dental prosthesis portions, the at least one connecting segment being surrounded by the body of the dental prosthesis, the dental prosthesis portions being spaced-apart from one another with a portion of the body of the removable dental prosthesis extending between adjacent ones of the dental prosthesis portions, each one of the dental prosthesis portions comprising a dental prosthesis sleeve open at one end and closed at an opposed end and defining an inner cavity and having a central axis, the dental prosthesis sleeve comprising an outer rigid sleeve and an inner flexible sleeve removably fitted in the outer rigid sleeve, the inner flexible sleeve defining an inner peripheral wall having at least one of a protrusion and a recess, the inner cavities of the dental prosthesis sleeves having a closed figure shape access port at the open end and opened in and accessible through the gum receiving cavity of the removable dental prosthesis, the central axes of the open-ended dental prosthesis sleeves extending substantially parallel to one another; and a plurality of dental implant portions securable to at least one endosseous dental implant and removably engageable with the dental prosthesis portions, each one of the dental implant portions comprising an attachment pillar having a central axis and being removably insertable within the inner cavity of a corresponding one of the dental prosthesis sleeves and being retained in the inner cavity by a friction fit, the central axes of the attachment pillars extending substantially parallel to one another.

16. A method for designing a dental prosthesis system, the method comprising the steps of:

obtaining a model of a patient's mouth including dental implants;

determining an implant orientation for each one of the patient's dental implants;

determining a correction orientation for each one of the dental implants, the correction orientation corresponding to a difference between the implant orientation and an aligned orientation of each one of the dental implants, the aligned orientation being an orientation at which the dental implants extend substantially parallel to one another;

designing an implant abutment for each one of the dental implants, each one of the implant abutments comprising a body with a base portion extending along a base portion axis and a head portion extending along a head portion axis, the base portion being securable to a respective one of the dental implants, wherein, for each one of the implant abutments, an angle between the head portion axis and the base portion axis corresponds to a respective one of the correction orientations; and designing a dental prosthesis comprising a body defining a gum receiving cavity and having a plurality of dental prosthesis portions and at least one connecting segment physically connecting a respective one of the dental prosthesis portion to an adjacent one of the dental prosthesis portions, the at least one connecting segment being surrounded by the body of the dental prosthesis, each one of the dental prosthesis portions being associated to a corresponding one of the implant abutments and comprising a dental prosthesis sleeve having a central axis and an inner cavity extending between an open end and a closed end, wherein designing the dental prosthesis further comprises aligning each one of the dental prosthesis sleeves with the corresponding one of the implant abutments with the central axes of the dental prosthesis sleeves extending substantially parallel to one another with the inner cavities being accessible through the open end opened in the gum receiving cavity of the dental prosthesis for removably engaging with the head portion of the corresponding one of the implant abutments.

17. A removable dental prosthesis comprising:
a dental prosthesis body with a gum receiving cavity; and
an attachment bar permanently embedded within the dental prosthesis body, the attachment bar comprising a plurality of spaced-apart dental prosthesis portions and at least one connecting segment extending between adjacent ones of the dental prosthesis portions, the at least one connecting segment being secured to respective outer surfaces of the adjacent ones of the dental prosthesis portions, the at least one connecting segment being surrounded by the dental prosthesis body, each one of the plurality of dental prosthesis portions comprising a dental prosthesis sleeve with an inner peripheral wall defining an inner cavity extending between an open end and a closed end, the inner cavities of the dental prosthesis sleeves being spaced-apart from one another and having a closed figure shape access port in the open end and opened in the gum receiving cavity of the removable dental prosthesis when the attachment bar is embedded therein.

18. The removable dental prosthesis according to claim 17, wherein the outer surfaces of the dental prosthesis portions comprise outwardly extending pillar base abutment flanges abutting against dental implant portions including the attachment pillars when the attachment pillars are engaged with the dental prosthesis portions.

19. The removable dental prosthesis as claimed in claim 17, wherein each one of the inner cavities comprises an outer rigid sleeve and an inner flexible sleeve removably fitted in the outer rigid sleeve, the inner flexible sleeve being made of a retention material, the inner flexible sleeve defining the inner peripheral wall and having at least one of a protrusion and a recess configured to removably interlock with an attachment pillar having a corresponding at least one of a protrusion and a recess.

20. The removable dental prosthesis according to claim 17, wherein the inner cavities of the dental prosthesis sleeves extend substantially parallel to one another.

21. The removable dental prosthesis according to claim 17, wherein the outer surfaces of the dental prosthesis portions are surrounded by the dental prosthesis body.

* * * * *